US009493766B2

(12) United States Patent
Peng et al.

(10) Patent No.: US 9,493,766 B2
(45) Date of Patent: Nov. 15, 2016

(54) PCR REACTION CLEANUP BUFFERS

(71) Applicant: CORNING INCORPORATED, Corning, NY (US)

(72) Inventors: Jinlin Peng, Painted Post, NY (US); Thomas Mark Leslie, Horseheads, NY (US)

(73) Assignee: Corning Incorporated, Corning, NY (US)

(*) Notice: Subject to any disclaimer, the term of this patent is extended or adjusted under 35 U.S.C. 154(b) by 0 days.

(21) Appl. No.: 14/169,959

(22) Filed: Jan. 31, 2014

(65) Prior Publication Data

US 2014/0220581 A1 Aug. 7, 2014

Related U.S. Application Data

(60) Provisional application No. 61/760,375, filed on Feb. 4, 2013.

(51) Int. Cl.
*C12N 15/10* (2006.01)
*C12Q 1/68* (2006.01)

(52) U.S. Cl.
CPC ......... *C12N 15/1013* (2013.01); *C12Q 1/6806* (2013.01)

(58) Field of Classification Search
CPC ............... C12N 15/1013; C12Q 2527/125
USPC .......................................... 568/623; 435/6.1
See application file for complete search history.

(56) References Cited

U.S. PATENT DOCUMENTS

| 5,705,623 A | 1/1998 | Wiggins et al. |
| 2012/0123106 A1 | 5/2012 | Joos |
| 2013/0143909 A1* | 6/2013 | Chong ............. A61K 47/48215 514/283 |

FOREIGN PATENT DOCUMENTS

| WO | 2004009851 | 1/2004 |
| WO | 2005089929 | 9/2005 |
| WO | 2012069660 | 5/2012 |

OTHER PUBLICATIONS

Deangelis et al, "Solid-Phase Reversible Immobilization for the Isolation of PCR Products"; Nucleic Acids Research, 1995, vol. 23, No. 22 pp. 4742-4743.
U.S. Appl. No. 61/666,138 Application and Drawings.
Perstorp: "Product Data Sheet Polyol 3165" Dec. 28, 2011.
Chomczynski et al; "Alkaline Polyethylene Glycol-Based Method for Direct PCR From Bacteria, Eukaryotic Tissue Samples, and Whole Blood"; Biotechniques 40:454-458 Apr. 2006.
PCT/US2014/014518 Search Report.

* cited by examiner

*Primary Examiner* — Jezia Riley
(74) *Attorney, Agent, or Firm* — Susan S. Wilks; David Casimir

(57) ABSTRACT

The present disclosure relates to buffers containing polyols for use with affinity-binding and/or magnetically susceptible thermoplastic particles and methods of making and use thereof.

13 Claims, 4 Drawing Sheets

Figure 4. Buffer evaluation with SMA magnetic particles, All Buffers contains 2.5M NaCl, 1xTE, 10mg/ml 15M30F particle were used. : *SM_B1*: 30% PEG 600, *SM_B2*, 40% 3165, *SM_B3* 40% 4800, *SM_B4* 40% R6405, *SM_B5*, 40% R3215, *SM_B6* 40% 4640 and *SM_B4290*_40%B4290, *Axygen* Original product solution

PCR REACTION CLEANUP BUFFERS

This application claims the benefit of priority under 35 U.S.C. §119 of U.S. Provisional Application Ser. No. 61/760,375 filed on Feb. 4, 2013 the content of which is relied upon and incorporated herein by reference in its entirety.

TECHNICAL FIELD

The present disclosure relates to buffers for use with affinity-binding and/or magnetically susceptible thermoplastic particles and methods of making and use thereof.

BACKGROUND

Isolation of biomolecules, such as nucleic acids and proteins, and the biological systems with which they are associated, such as cells and viruses, is a fundamental approach in biological research. Isolation provides a basis for characterizing biomolecules, toward understanding structure and function, and for observing, cultivating, and conducting experiments and tests on biological systems.

One method of isolation is based on use of a solid phase coupled with a ligand having an affinity for a particular biomolecule. The solid phase can be contacted with a substance including the biomolecule, such that the biomolecule binds the affinity ligand. Then the solid phase can be separated from the substance, accomplishing isolation of the biomolecule and/or biological systems associated therewith, from the substance. An example of such a solid phase is a particle configured both to include an affinity ligand on its surface, for binding a biomolecule, and to be attracted to a magnetic field, for subsequent separation to form a magnetic affinity-binding thermoplastic particle extraction process.

Binding of a biomolecule to an affinity ligand may be optimized with the use of specific buffer solutions. Polyethylene glycol (PEG) has been used in combination of salts to create useful buffers, often referred to as "crowding" buffers. However, polyethylene glycol is viscous and can be difficult to wash away from biomolecules of interest. Thus, there is a need for buffers that can be used for isolation of biomolecules and the biological systems associated therewith using magnetic affinity-binding thermoplastic particle extraction processes that are easy to wash away and/or are environmentally friendly.

SUMMARY

In embodiments, the disclosure provides a buffer solution for use with a magnetic affinity-binding thermoplastic particle extraction process comprising a polyol as defined below.

In an aspect (1), the disclosure provides a buffer for use with a magnetic affinity-binding thermoplastic particle extraction process comprising at least one soluble polyol having a base structure of Formula 3:

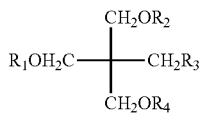

wherein R3 is OH, $CH_3$, $(-OCH_2CH_2O)_nH$;

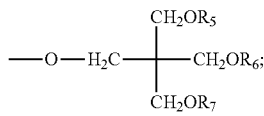

wherein R1, R2, R4, R5, R6 and R7 are each independently H, or $(-CH_2CH_2O)_nH$;
wherein each n is independently an integer of one or greater;
wherein at least one of R1, R2, R4, R5, R6 and R7 is $(-CH_2CH_2O)_nH$;
wherein the total number of $(-CH_2CH_2O)_nH$ groups is $N_t$; and,
wherein $N_t$ is at least 6.

In an aspect (2), the disclosure provides the buffer of aspect 1 wherein the polyol is alkoxylated pentaerythritol or alkoxylated trimethylolpropane.

In an aspect (3), the disclosure provides the buffer of aspect (2), wherein the polyol is alkoxylated pentaerythritol or alkoxylated trimethylolpropane.

In an aspect (4), the disclosure provides the buffer of aspect 1, further comprising magnetic beads.

In an aspect (5), the disclosure provides a use of the buffer of aspect 4, comprising: contacting a substance comprising a biomolecule with the buffer solution of claim 1 such that the solid phase binds the biomolecule through a derivative functional group on the surface of the magnetic beads; and isolating the biomolecule from the substance.

In an aspect (6), the disclosure provides a buffer for use with a magnetic affinity-binding thermoplastic particle extraction process comprising at least one soluble polyol having a base structure of:

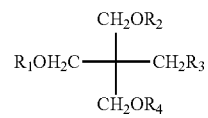

wherein R3 is OH, $CH_3$, $(-OCH_2CH_2O)_nH$;

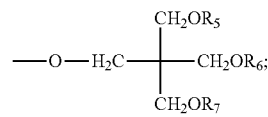

wherein R1, R2, R4, R5, R6 and R7 are each independently H, or $(-CH_2CH_2O)_nH$;
wherein each n is independently an integer of one or greater;
wherein the total number of $(-CH_2CH_2O)_n$ groups is $N_t$;
wherein the polyol has more than two terminal OH groups and
wherein the ratio of terminal OH groups to $N_t$ is greater than 2:1.

In an aspect (7), the disclosure provides the buffer of aspect 6 wherein $N_t$ is at least 6.

In an aspect (8), the disclosure provides the buffer of aspect 6 wherein the polyol is alkoxylated pentaerythritol or alkoxylated trimethylolpropane.

In an aspect (9), the disclosure provides the buffer of aspect 7 wherein the polyol is alkoxylated pentaerythritol or alkoxylated trimethylolpropane.

In an aspect (10), the disclosure provides the buffer of aspect 6 further comprising magnetic beads.

In an aspect (11), the disclosure provides the buffer of aspect 7 further comprising magnetic beads In an aspect (12), the disclosure provides a method of use of the buffer phase of aspect 6, comprising: contacting a substance comprising a biomolecule with the buffer solution of claim 1 such that the solid phase binds the biomolecule through a derivative functional group on the surface of the magnetic beads; and isolating the biomolecule from the substance.

In an aspect (13), the disclosure provides a method of use of the buffer phase of claim 7, comprising: contacting a substance comprising a biomolecule with the buffer solution of claim 1 such that the solid phase binds the biomolecule through a derivative functional group on the surface of the magnetic beads; and isolating the biomolecule from the substance.

BRIEF DESCRIPTION OF THE DRAWINGS

These and other aspects are better understood when the following detailed description is read with reference to the accompanying drawings.

DETAILED DESCRIPTION

Figure 1:
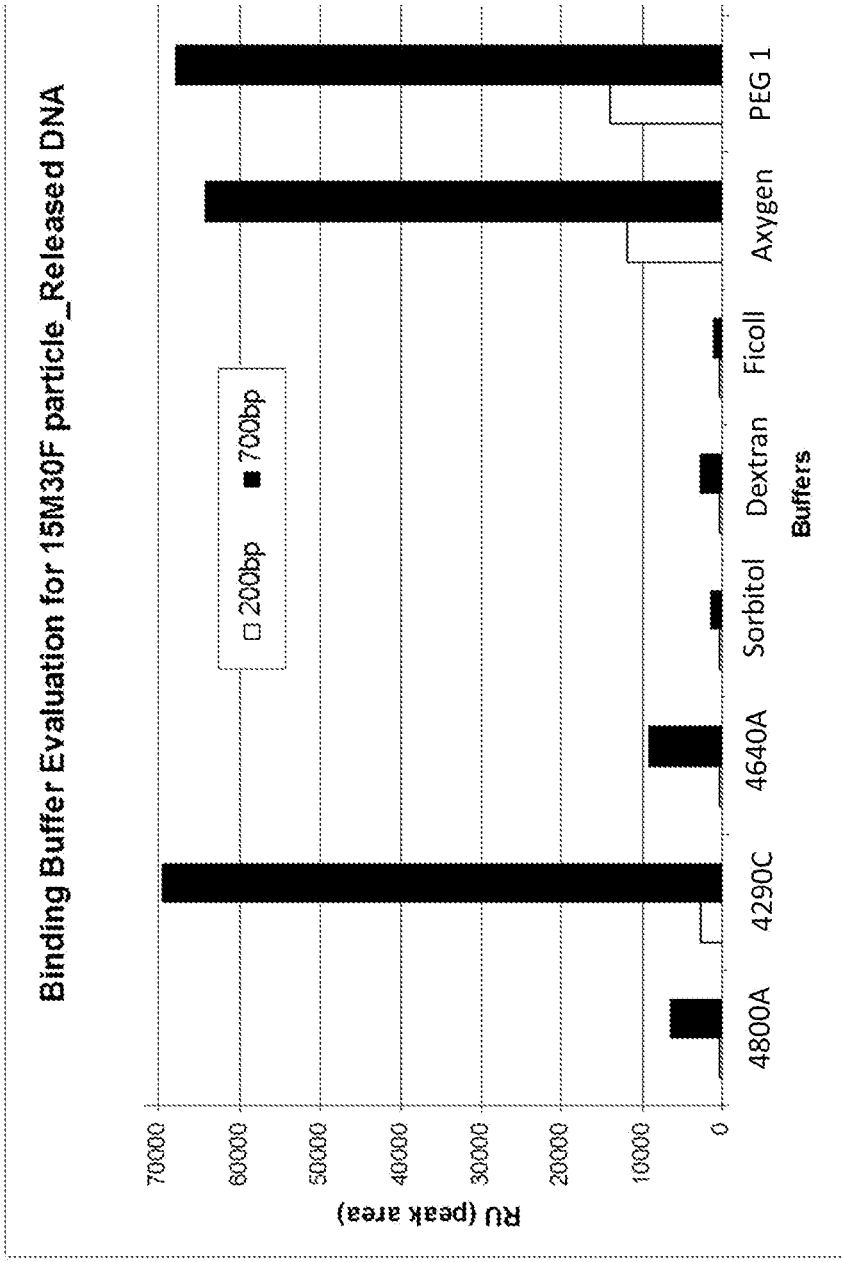
FIG. 1 is a graph showing binding buffer performance showing released DNA (measured in RU on the Y axis) with SMA magnetic particles for experimental solutions as defined in Tables 1, 2 and 3, and a commercially available buffer, available from Axygen, Foster City, Calif., (Axygen).

Examples will now be described more fully hereinafter with reference to the accompanying drawings in which example embodiments are shown. Whenever possible, the same reference numerals and/or symbols are used throughout the drawings to refer to the same or like parts. However, aspects may be embodied in many different forms and should not be construed as limited to the embodiments set forth herein.

As set forth in the figures, example buffers for use with a magnetic affinity-binding thermoplastic particle extraction process comprising alkoxylated pentaerythritol or alkoxylated trimethylolpropane are provided. Thermoplastic solid phase particles are shown, in examples. The thermoplastic solid phase particles with a specific surface chemistry that interacts with a biomolecule such as DNA are provided in a buffer solution. While one application is the purification of DNA made in a PCR reaction, the thermoplastic particle may be coated with any affinity ligand suitable for extraction of any biological material from a mixed material. These include but are not limited to, extraction of plant DNA from ground up plant material, Buccal Swabs contaminated with cell debris, DNA from Blood and so forth. All of these sources of DNA are a mixture of proteins and other biological entities that need to be removed from the DNA before it can be used. As an example, a PCR reaction product contains a mixture of DNA, polymerase enzyme, DNA primers, nucleotide building blocks and other impurities when finished. In all cases, the buffer containing magnetically susceptible microparticles is used to extract a biological material from the rest of the biological impurities.

Polyethylene glycol or PEG, combined with appropriate salts has been used for the purification of DNA made in a PCR reaction. Buffers may be supplied as a "Kit" to the customer as a formulated suspension with written instructions for ease of use. Polyethylene glycol (PEG) with salt has been described as a "crowding" buffer system used for this application. A crowding buffer is a buffer system that crowds out the biological entity by gathering or tying up water. PEG and salt both want to be highly hydrated therefore gathering the water to themselves, thereby "crowding out" biological material, and improving the efficiency of a purification process.

Multifunctional alcohols, known as a polyol, specifically "alkoxylated pentaerythritol" or "alkoxylated trimethylolpropane" are used as multifunctional crosslinkers in polyurethane formulations. The manufactures data sheet classifies them as multifunctional alkoxylated polyols with primary alcohols. When acrylate moieties are attached to the alcohol moieties, the material is used as a multifunctional crosslinker in radical initiated polymerizations for coatings. It is also known as a general chemical building block. These multifunctional alcohols are small compared to PEG which may have a molecular weight of around 8,000. One unsuspected benefit of this small size multifunctional alcohol over PEG as the crowding agent is that they lower buffer viscosity. These materials are not polymers, and have different physical properties compared to polymers such as PEG. Viscosity, for example, is lower. These smaller materials wash away more easily allowing for more rapid mixing and magnetic extraction. This lower viscosity allows for the buffer to be more easily washed away from the magnetic bead pellet after DNA extraction. It may also improve the ability of the magnetically susceptible particles to capture DNA because of the lower buffer viscosity. Preliminary results show that varying the concentration of the polyol may allow for a controlled extraction of DNA based on the size of DNA that will attach to magnetic particles in the buffer system.

In embodiments, the buffer for use with a magnetic affinity-binding thermoplastic particle extraction process comprises at least one soluble polyol made from two units: (1) a base structure as shown in Formula 1 (CAS #115-77-5, $C(CH_2OH)_4$ 1,3 Propanediol):

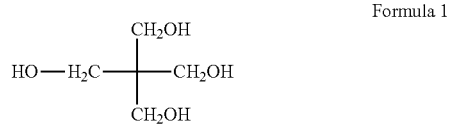

Formula 1 and (2) a component having the structure shown in Formula 2 (CAS #75-21-8, $C_2H_4O$, Oxirane) wherein the ratio of the composition of Formula 2:the composition of Formula 1 is at least 1:1.

Formula 2

When the ring structure of Formula 2 is opened, Formula 2 can also be written as (—OCH$_2$CH$_2$O)$_n$H. Another way to describe the materials are as Pentaerythritol ethoxylates with substituted arms. For example, the base structure of Formula 1 can be substituted as shown in Formula 3:

Formula 3

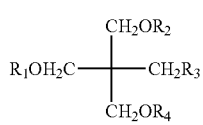

wherein R3 is OH, CH$_3$, (—OCH$_2$CH$_2$O)$_n$H, or the structure shown in Formula 4.

Formula 4

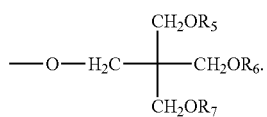

wherein R1, R2, R4, R5, R6 and R7 are each independently H, or (—CH$_2$CH$_2$O)$_n$H; wherein each n is independently an integer of one or greater; wherein at least one of R1, R2, R4, R5, R6 and R7 is (—CH$_2$CH$_2$O)$_n$H; wherein the total number of (—CH$_2$CH$_2$O)$_n$H groups is N$_t$; and wherein N$_t$ is at least 6.

The structure of Formula 2, in its open ring configuration, is (—OCH$_2$CH$_2$O)$_n$H (an ethylene oxide arm, or an EO arm). In embodiments, a polyol can be made from a mixture of ethylene oxide arms (the structure of Formula 2) with the base structure of Formula 3. Ethylene oxide arms will bond with available hydroxy groups (OH groups), or with each other to form branched structures having a ratio of ethylene oxide groups to the core structure, depending upon the ratio of the base structure (of Formula 3) to the ratio of the ethylene groups (Formula 2) that are reacted together.

The core structure (Formula 3) may be substituted. For example, in Table 1 below, the core structure of POLYOL 3165 is shown (Polyol 3165, available from Perstorp Holding AB Sweden). POLYOL 3165 can be described as the base structure shown in has three OH substitutions at R1, R2 and R4. R3 is CH$_3$. The total number of ethylene oxide groups can be calculated based on the molecular weight of the material. For example, for the ethylene oxide groups, (—CH$_2$CH$_2$O)$_n$H, the total value for "n" (N$_t$) can be calculated by subtracting the molecular weight of the core (Formula 3, substituted as described above, and as shown in Table 1) from the reported molecular weight of the polyol (as reported by the manufacturer) and dividing that result by 44, the molecular weight of ethylene oxide. These calculations of N$_t$ are shown in Table 1. The N$_t$ value can also be expressed as a ratio of N$_t$:number of available OH groups. This is shown in Table 1 as N$_t$/OH. For example, for Buffer 3215, which includes polyol 3215, the N$_t$/OH ratio is 15/3. Because ethylene oxide groups are mixed with the base structure (which can have three, four or six OH groups, as shown in Table 1) at a ratio of ethylene oxide to base structure, the ethylene oxide groups may attach randomly to available OH groups, or each other. While it is possible to calculate the N$_t$ and the N$_t$/OH ratio, it is not possible to thoroughly describe the random array of ethylene oxide groups that may be present in a polyol. Therefore, the total number of ethylene oxide groups, compared to the base structure, or compared to the number of available OH groups on the substituted base structure, or the N$_t$/OH ratio, are appropriate descriptions of the polyol structure. Another way to describe these buffers is to discuss them in terms of their total number of ethylene oxide substitutions, or Nt.

These compositions are also known as PERSTORP POLYOLS available from Perstorp (Perstorp Holding AB Sweden). For example, the structures shown below can be purchased from Perstorp as numbered polyols (polyol 3165, polyol 4800, polyol R6405, polyol 4640 and polyol 4290 with the structures shown In Table 1 below. These materials can be obtained from other suppliers such as Sigma Aldrich. In each case, the polyol is purchased as a mixture of the base structure of Formula 3 and the ethylene oxide structure of Formula 2 (also described, when the ring is opened, as occurs in aqueous solution, as (—CH$_2$CH$_2$O)$_n$H).

Exemplary structures are shown in Table 1:

TABLE 1

| Polyol | Structure | g/mol | viscosity in cps | Nt | OH | N$_t$/OH |
|---|---|---|---|---|---|---|
| 3165 | HO—(H$_2$C—H$_2$C—O)$_{n3}$—H$_2$C—C(CH$_2$—(O—CH$_2$—CH$_2$)$_{n1}$—OH)(CH$_2$—CH$_3$)(CH$_2$—(O—CH$_2$—CH$_2$)$_{n2}$—OH) | 1014 | 350 | 20 | 3 | 20/3+ |
| R6405 | HO—(H$_2$C—H$_2$C—O)$_{n1}$—CH$_2$, HO—(H$_2$C—H$_2$C—O—C$_{H_2}$)$_{n6}$—H$_2$C—O—H$_2$C—C(CH$_2$—(O—CH$_2$—CH$_2$)$_{n2}$—OH)(CH$_2$—(O—CH$_2$—CH$_2$)$_{n3}$—OH)(CH$_2$—(O—CH$_2$—CH$_2$)$_{n4}$—OH), HO—(H$_2$C—H$_2$C—O)$_{n5}$—CH$_2$ | 827 | 1900 | 13 | 6 | 13/6+ |

TABLE 1-continued

| Polyol | Structure | g/mol | viscosity in cps | Nt | OH | $N_t/OH$ |
|---|---|---|---|---|---|---|
| R3215 | HO—[H$_2$C—H$_2$C—O]$_{n3}$—H$_2$C—C(—CH$_2$—[O—CH$_2$—CH$_2$]$_{n1}$—OH)(—CH$_2$—CH$_3$)(—CH$_2$—[O—CH$_2$—CH$_2$]$_{n2}$—OH) | 795 | 340 | 15 | 3 | 11/3+ |
| 4640 | HO—[H$_2$C—H$_2$C—O]$_{n1}$—H$_2$C—C(—CH$_2$—[O—CH$_2$—CH$_2$]$_{n2}$—OH)(—CH$_2$—[O—CH$_2$—CH$_2$]$_{n3}$—OH)(—CH$_2$—[O—CH$_2$—CH$_2$]$_{n4}$—OH) | 355 | 1100 | 5 | 4 | 5/4− |
| 4290 | HO—[H$_2$C—H$_2$C—O]$_{n1}$—H$_2$C—C(—CH$_2$—[O—CH$_2$—CH$_2$]$_{n2}$—OH)(—CH$_2$—[O—CH$_2$—CH$_2$]$_{n3}$—OH)(—CH$_2$—[O—CH$_2$—CH$_2$]$_{n4}$—OH) | 797 | 450 | 15 | 4 | 11/4+ |
| 4800 | HO—[H$_2$C—H$_2$C—O]$_{n1}$—H$_2$C—C(—CH$_2$—[O—CH$_2$—CH$_2$]$_{n2}$—OH)(—CH$_2$—[O—CH$_2$—CH$_2$]$_{n3}$—OH)(—CH$_2$—[O—CH$_2$—CH$_2$]$_{n4}$—OH) | 282 | 2200 | 3.4 | 4 | 3.4/4− |
| 4360 | HO—[HC(CH$_3$)—H$_2$C—O]$_{n1}$—H$_2$C—C(—CH$_2$—[O—CH$_2$—CH(CH$_3$)]$_{n2}$—OH)(—CH$_2$—[O—CH$_2$—CH(CH$_3$)]$_{n3}$—OH)(—CH$_2$—[O—CH$_2$—CH(CH$_3$)]$_{n4}$—OH) | 629 | 1300 | 8.5 | 4 | *8.5/4 |

The buffers used in the examples disclosed herein are shown in Table 2 and Table 3.

TABLE 2

| Buffer | PEG | Structure |
|---|---|---|
| PEG 1<br>2.5 NaCl, 1xTE<br>20% PEG in H$_2$O | PEG (8000)<br>mw = 600 | HO—[CH$_2$—CH$_2$—O]$_{n\sim10}$—H |
| PEG 2<br>2.5 NaCl, 1xTE<br>30% PEG in H$_2$O | PEG (8000)<br>mw = 600 | HO—[CH$_2$—CH$_2$—O]$_{n\sim10}$—H |
| PEG 3<br>2.5 NaCl, 1xTE<br>40% PEG in H$_2$O | PEG (8000)<br>mw = 600 | HO—[CH$_2$—CH$_2$—O]$_{n\sim10}$—H |

TABLE 3

| Buffer | Polyol | Structure |
|---|---|---|
| 3165A<br>2.5 NaCl,<br>1xTE<br>30% Polyol 3165<br>in H$_2$O | Polyol 3165<br>Trimethylol-<br>propane<br>ethoxylate<br>(Nt/OH = 20/3) | HO—[H$_2$C—H$_2$C—O]$_{n3}$—H$_2$C—C(—CH$_2$—[O—CH$_2$—CH$_2$]$_{n1}$—OH)(—CH$_2$—CH$_3$)(—CH$_2$—[O—CH$_2$—CH$_2$]$_{n2}$—OH) |

TABLE 3-continued

| Buffer | Polyol | Structure |
|---|---|---|
| 3165B 2.5 NaCl, 1xTE 40% Polyol 3165 in H$_2$O | Polyol 3165 Trimethylol- propane ethoxylate (Nt/OH = 20/3) | HO—(H$_2$C—H$_2$C—O)$_{n3}$—H$_2$C—C(—CH$_2$(O—CH$_2$—CH$_2$)$_{n1}$—OH)(—CH$_2$—CH$_3$)(—CH$_2$(O—CH$_2$—CH$_2$)$_{n2}$—OH) |
| 4800A 2.5 NaCl, 1xTE 30% Polyol 4800 in H$_2$O | Polyol 4800 (Pentaeryth- ritol ethoxylate (Nt/OH = 3.4/4) | HO—(H$_2$C—H$_2$C—O)$_{n1}$—H$_2$C—C(—CH$_2$(O—CH$_2$—CH$_2$)$_{n2}$—OH)(—CH$_2$(O—CH$_2$—CH$_2$)$_{n3}$—OH)(—CH$_2$(O—CH$_2$—CH$_2$)$_{n4}$—OH) |
| 4800B 2.5 NaCl, 1xTE 40% Polyol 4800 in H$_2$O | Polyol 4800 (Pentaeryth- ritol ethoxylate (Nt/OH = 3.4/4) | HO—(H$_2$C—H$_2$C—O)$_{n1}$—H$_2$C—C(—CH$_2$(O—CH$_2$—CH$_2$)$_{n2}$—OH)(—CH$_2$(O—CH$_2$—CH$_2$)$_{n3}$—OH)(—CH$_2$(O—CH$_2$—CH$_2$)$_{n4}$—OH) |
| R6405A 2.5 NaCl, 1xTE 30% Polyol R6405 in H$_2$O | Polyol R6405 (Nt/OH = 13/6) | HO—(CH$_2$—CH$_2$—O)$_{n1}$—CH$_2$— ; HO—(CH$_2$—CH$_2$—O—CH$_2$)$_{n6}$—H$_2$C—O—H$_2$C—C(—CH$_2$(O—CH$_2$—CH$_2$)$_{n2}$—OH)(—CH$_2$(O—CH$_2$—CH$_2$)$_{n3}$—OH)(—CH$_2$(O—CH$_2$—CH$_2$)$_{n4}$—OH) ; HO—(CH$_2$—CH$_2$—O)$_{n5}$—CH$_2$— |
| R6405B 2.5 NaCl, 1xTE 40% Polyol R6405 in H$_2$O | Polyol R6405 (Nt/OH = 13/6) | HO—(CH$_2$—CH$_2$—O)$_{n1}$—CH$_2$— ; HO—(CH$_2$—CH$_2$—O—CH$_2$)$_{n6}$—H$_2$C—O—H$_2$C—C(—CH$_2$(O—CH$_2$—CH$_2$)$_{n2}$—OH)(—CH$_2$(O—CH$_2$—CH$_2$)$_{n3}$—OH)(—CH$_2$(O—CH$_2$—CH$_2$)$_{n4}$—OH) ; HO—(CH$_2$—CH$_2$—O)$_{n5}$—CH$_2$— |
| R3215A 2.5 NaCl, 1xTE 30% Polyol R3215 in H$_2$O | Polyol R3215 Trimethylol- propane ethoxylate (Nt/OH = 15/3) | HO—(H$_2$C—H$_2$C—O)$_{n3}$—H$_2$C—C(—CH$_2$(O—CH$_2$—CH$_2$)$_{n1}$—OH)(—CH$_2$—CH$_3$)(—CH$_2$(O—CH$_2$—CH$_2$)$_{n2}$—OH) |
| R3215B 2.5 NaCl, 1xTE 40% Polyol R3215 in H$_2$O | Polyol R3215 Trimethylol- propane ethoxylate (Nt/OH = 15/3) | HO—(H$_2$C—H$_2$C—O)$_{n3}$—H$_2$C—C(—CH$_2$(O—CH$_2$—CH$_2$)$_{n1}$—OH)(—CH$_2$—CH$_3$)(—CH$_2$(O—CH$_2$—CH$_2$)$_{n2}$—OH) |
| 4640A 2.5 NaCl, 1xTE 30% Polyol 4640 in H$_2$O | Polyol 4640 Pentaeryth- ritol ethoxylate (Nt/OH = 5/4) | HO—(H$_2$C—H$_2$C—O)$_{n1}$—H$_2$C—C(—CH$_2$(O—CH$_2$—CH$_2$)$_{n2}$—OH)(—CH$_2$(O—CH$_2$—CH$_2$)$_{n3}$—OH)(—CH$_2$(O—CH$_2$—CH$_2$)$_{n4}$—OH) |

TABLE 3-continued

| Buffer | Polyol | Structure |
|---|---|---|
| 4640B 2.5 NaCl, 1xTE 40% Polyol 4640 in H$_2$O | Polyol 4640 Pentaerythritol ethoxylate (Nt/OH = 5/4) | HO─(H$_2$C─H$_2$C─O)$_{n1}$─H$_2$C─C(CH$_2$─(O─CH$_2$─CH$_2$)$_{n2}$─OH)(CH$_2$─(O─CH$_2$─CH$_2$)$_{n3}$─OH)(CH$_2$─(O─CH$_2$─CH$_2$)$_{n4}$─OH) |
| 4290A 2.5 NaCl, 1xTE 10% Polyol 4290 in H$_2$O | Polyol 4290 Pentaerythritol ethoxylate (Nt/OH = 15/4) | HO─(H$_2$C─H$_2$C─O)$_{n1}$─H$_2$C─C(CH$_2$─(O─CH$_2$─CH$_2$)$_{n2}$─OH)(CH$_2$─(O─CH$_2$─CH$_2$)$_{n3}$─OH)(CH$_2$─(O─CH$_2$─CH$_2$)$_{n4}$─OH) |
| 4290B 2.5 NaCl, 1xTE 20% Polyol 4290 in H$_2$O | Polyol 4290 Pentaerythritol ethoxylate (Nt/OH = 15/4) | HO─(H$_2$C─H$_2$C─O)$_{n1}$─H$_2$C─C(CH$_2$─(O─CH$_2$─CH$_2$)$_{n2}$─OH)(CH$_2$─(O─CH$_2$─CH$_2$)$_{n3}$─OH)(CH$_2$─(O─CH$_2$─CH$_2$)$_{n4}$─OH) |
| 4290C 2.5 NaCl, 1xTE 30% Polyol 4290 in H$_2$O | Polyol 4290 Pentaerythritol ethoxylate (Nt/OH = 15/4) | HO─(H$_2$C─H$_2$C─O)$_{n1}$─H$_2$C─C(CH$_2$─(O─CH$_2$─CH$_2$)$_{n2}$─OH)(CH$_2$─(O─CH$_2$─CH$_2$)$_{n3}$─OH)(CH$_2$─(O─CH$_2$─CH$_2$)$_{n4}$─OH) |
| 4290D 2.5 NaCl, 1xTE 40% Polyol 4290 in H$_2$O | Polyol 4290 Pentaerythritol ethoxylate (Nt/OH = 15/4) | HO─(H$_2$C─H$_2$C─O)$_{n1}$─H$_2$C─C(CH$_2$─(O─CH$_2$─CH$_2$)$_{n2}$─OH)(CH$_2$─(O─CH$_2$─CH$_2$)$_{n3}$─OH)(CH$_2$─(O─CH$_2$─CH$_2$)$_{n4}$─OH) |
| Polyol 4360* | Polyol 4360 (Nt/OH = 8.5/4) | HO─(HC(CH$_3$)─H$_2$C─O)$_{n1}$─H$_2$C─C(CH$_2$─(O─CH$_2$─CH(CH$_3$))$_{n2}$─OH)(CH$_2$─(O─CH$_2$─CH(CH$_3$))$_{n3}$─OH)(CH$_2$─(O─CH$_2$─CH(CH$_3$))$_{n4}$─OH) |
| Sorbitol 2.5 NaCl, 1xTE 20% in H$_2$O | n/a | CH$_2$OH─(H,H)─(HO,H)─(H,OH)─(H,OH)─CH$_2$OH |

TABLE 3-continued

| Buffer | Polyol | Structure |
|---|---|---|
| Dextran 2.5 NaCl, 1xTE 20% (100-200k) in H₂O | n/a | 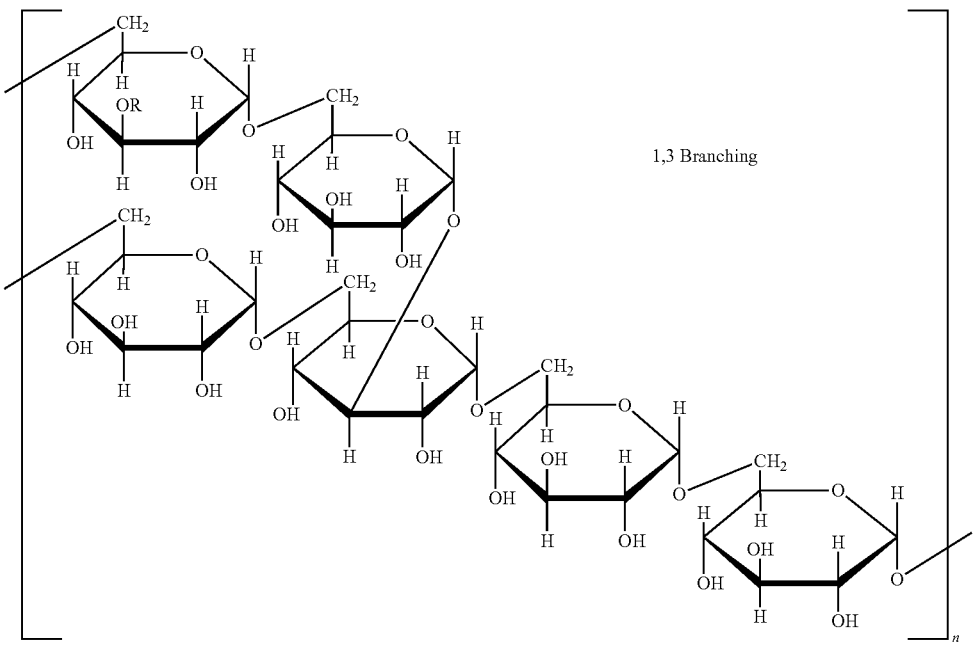 1,3 Branching |
| Ficoll 2.5 NaCl, 1xTE 20% in H₂O | n/a | 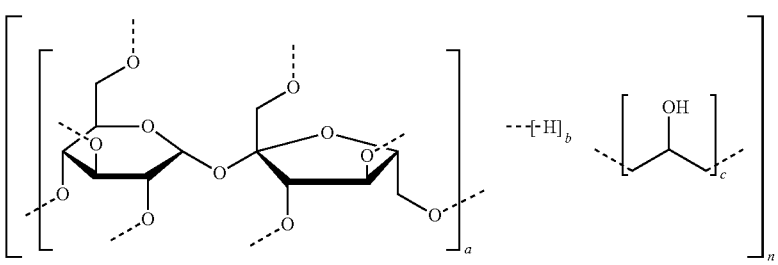 |

In embodiments, the disclosure provides a buffer for use with a magnetic affinity-binding thermoplastic particle extraction process comprising at least one soluble polyol having a base structure of Formula 3, wherein R1, R2, R4, R5, R6 and R7 are each independently H, or (—CH$_2$CH$_2$O)$_n$H; wherein each n is independently an integer of one or greater; wherein at least one of R1, R2, R4, R5, R6 and R7 is (—CH$_2$CH$_2$O)$_n$H; wherein the total number of (—CH$_2$CH$_2$O)$_n$H groups is N$_t$; and wherein N$_t$ is at least 6, wherein the total number of (—CH$_2$CH$_2$O)$_n$ groups is N$_t$; wherein the polyol has more than two terminal OH groups and wherein the ratio of terminal OH groups to N$_t$ is greater than 1:1.

Without being limited by theory, one advantage of using a low molecular weight material with a low viscosity rather than a solid high molecular weight polymer (such as PEG 8000, for example which is a solid at room temperature) is that the low molecular weight material dissolved into water generates a buffer with a higher viscosity at up to twice the polyol concentration over PEG. Buffers formulated with these polyols have significantly lower viscosity compared to buffers formulated with PEG. This lower viscosity allows for DNA and particles used to capture DNA to mix more easily. In addition, the lower viscosity buffer is more easily washed away from the magnetic beads after DNA extraction. The beads can be collected by a magnet more quickly due to the lower viscosity of the buffer solution. This characteristic may also improve the ability of the magnetically susceptible particles to capture DNA because the lower molecular weight DNA needs to displace the crowding agent from the surface of the particle. Preliminary results also show that by varying the concentration of the polyol in the binding buffer, selection of the size DNA that will attach to the particles may be possible. Note that Polyol4360 (shown with an asterix (*) in Tables 1 and 3) has a propylene oxide base structure, instead of an ethylene oxide base structure. This material was not soluble enough to provide in a high salt buffer solution suitable for the DNA extraction testing performed herein. In embodiments, "soluble" means that the polyol is soluble up to at least 30-40% in 2.5M salt (such as NaCl solution). For example, Polyol 4360 was not soluble.

EXAMPLES

Example 1

Magnetic Particles and Binding Buffer Preparation

Experimental DNA binding buffers added several Perstorp Polyols, "alkoxylated pentaerythritol" to the standard 20% by weight PEG 8,000 mw dissolved into a 2.5 molar sodium chloride solution as the DNA binding buffer (PEG/ salt binding buffers are described if, for example, U.S. Pat. No. 5,705,628, and *Solid-phase reversible immobilization for the isolation of PCR products*, Margaret M. DeAngelis, David G. Wang and Trevor L. Hawkins, Nucleic Acids Research, 1995, Vol. 23, No. 22, pp 4742-4743). The experimental buffer system currently used 2.5 molar sodium chloride and 10-40% Perstorp Polyols such as polyol 4290, polyol 4840, polyol 4640, polyol R3215 and polyol R6405 as the water grabbing/attracting additives. 10 mM tris and 1 mM EDTA were also included in the binding buffer mixture. Both commercially available beads (Axygen, Foster City, Calif.) and proprietary SMA magnetic particles produced in-house (see, for example, U.S. Patent Application 61/666,138 filed Jun. 29, 2012, and incorporated herein by reference in its entirety) were used in these experiments. For Axygen beads suspended in our polyol based buffers, the standard aliquot required for PCR cleanup of kit buffer was measured out and the beads were pulled over to the side of the PCR isolation tube. The kit buffer was removed, the beads washed, air dried and the same volume of our in-house Polyol binding solutions added to replace the kit buffer. This insured the same bead concentration was maintained as the original kit. For the SMA magnetic particles, 15M30F particles were used at a concentration of 10 mg/ml for all the binding buffers tested.

Example 2

PCR Reaction and Cleanup Protocol

Two PCR reactions were used to generate both the 200 bp and 700 bp fragments using standard PCR kits. The two PCR reactions were mixed 1:1 (v/v), to produce a PCR mixture containing both 200 bp and 700 bp fragments. The following protocol was used for all cleanup evaluations: (1) 20 ul total of the crude PCR solution was pipetted into a 1 ml tube, 36 ul magnetic beads/particle solution was then added and mixed; (2) After allowing 5 min for binding, the beads/particles solutions were put on a magnet for 2-5 min, the supernatant was collected with a pipette and discarded; (3) While the beads/particle were still on the magnet, it was washed 2× with a 70% alcohol solution (200 ul each) and the alcohol washes discarded (4) The captured DNA were eluded by adding 40 ul of 1× TE buffer.

Example 3

UPLC Analysis of the Eluded DNA Fragments

The eluted DNA from the magnetic beads/particles were identified and quantitated by UPLC analysis on a C18 reverse phase column, using the Waters UPLC system. Both the 200 bp and 700 bp DNA fragments were detected and quantitated in the UV at 260 nm using the Waters PDA detector. 10 ul of eluded DNA solution for each sample was injected for comparison. The yields of eluded DNA were based on the peak area for both the 200 bp and 700 bp DNA fragments. The UPLC also detects any residual DNA primers used for the reaction and no primers were seen after cleanup.

Considering features of buffers for magnetic affinity-binding thermoplastic solid phase extractions in more detail, FIGS. 1-4 provide graph showing binding buffer performance showing released DNA (measured in RU on the Y axis) isolated using magnetic particles for experimental solutions B1, B2, B3, B4, B5 and B6 (as defined in Table 1), an Axygen buffer and a PEG buffer.

FIG. 1 is a graph showing binding buffer performance showing released DNA (measured in RU on the Y axis) with SMA magnetic particles for experimental solutions as defined in Tables 1, 2 and 3, and a commercially available buffer, available from Axygen, Foster City, Calif., (Axygen). FIG. 1 shows that Buffer 4290C, containing a polyol having an Nt/OH ratio of 15/4, performed consistently with Axygen and PEG 1 controls. Buffers 4800A and 4640A, having an Nt/OH ratio of 3.4/4 and 5/4 respectively, did not perform. Described another way, Buffer 4290C, containing a polyol with an Nt of at least 6, performed. Buffers 4800A and 4640A, having Nt of 3.4 and 5 respectively, did not perform. Additional control buffer solutions including materials having OH groups but no ethylene oxide groups, sorbitol, dextran and FICOLL® (available from GE Healthcare, Piscataway, N.J.) were negative controls.

Figure 2:
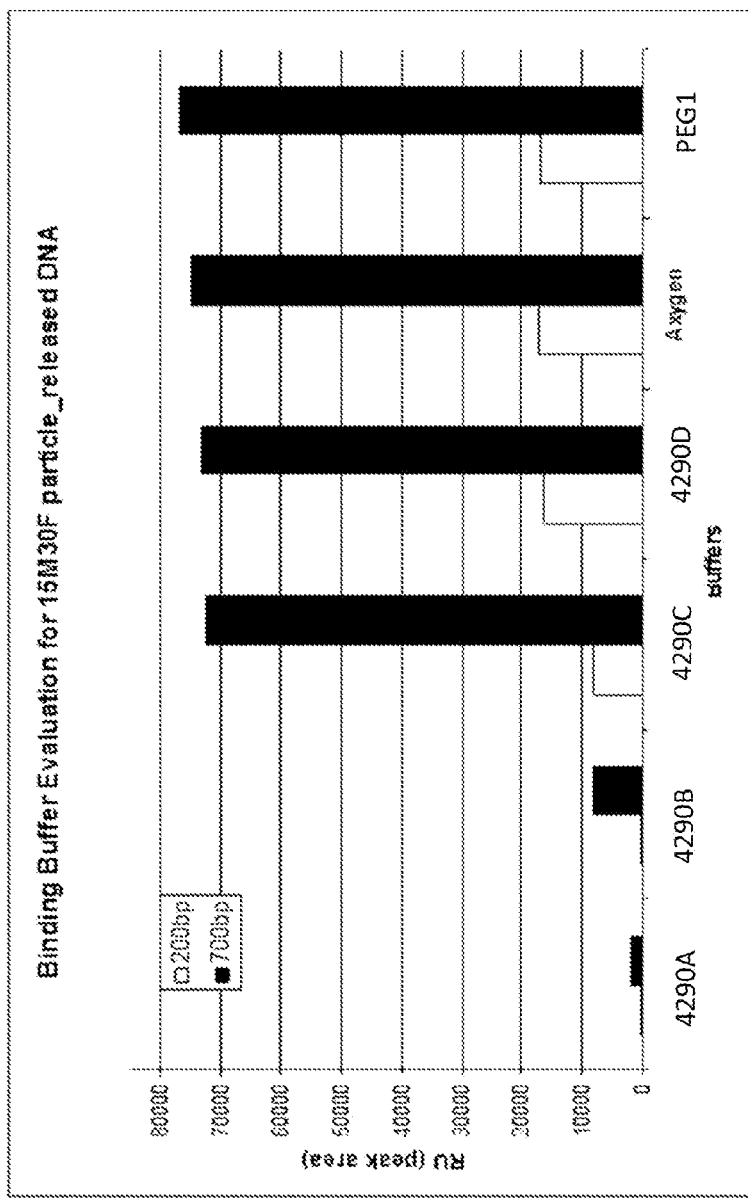
FIG. 2 is a graph showing binding buffer performance of the buffers defined in Tables 1, 2 and 3 and an Axygen buffer and a PEG buffer, showing released DNA (measured in RU on the Y axis).

FIG. 2 is a graph showing binding buffer performance of the 4290 buffers defined in Tables 1, 2 and 3 compared to a commercially available buffer from Axygen (Foster City, Calif.) the "Axygen buffer" and a PEG 1 buffer (as defined in Table 2) showing released DNA (measured in RU on the Y axis). FIG. 2 shows that the 4290 polyol behaves in a dose-dependent manner.

Figure 3:
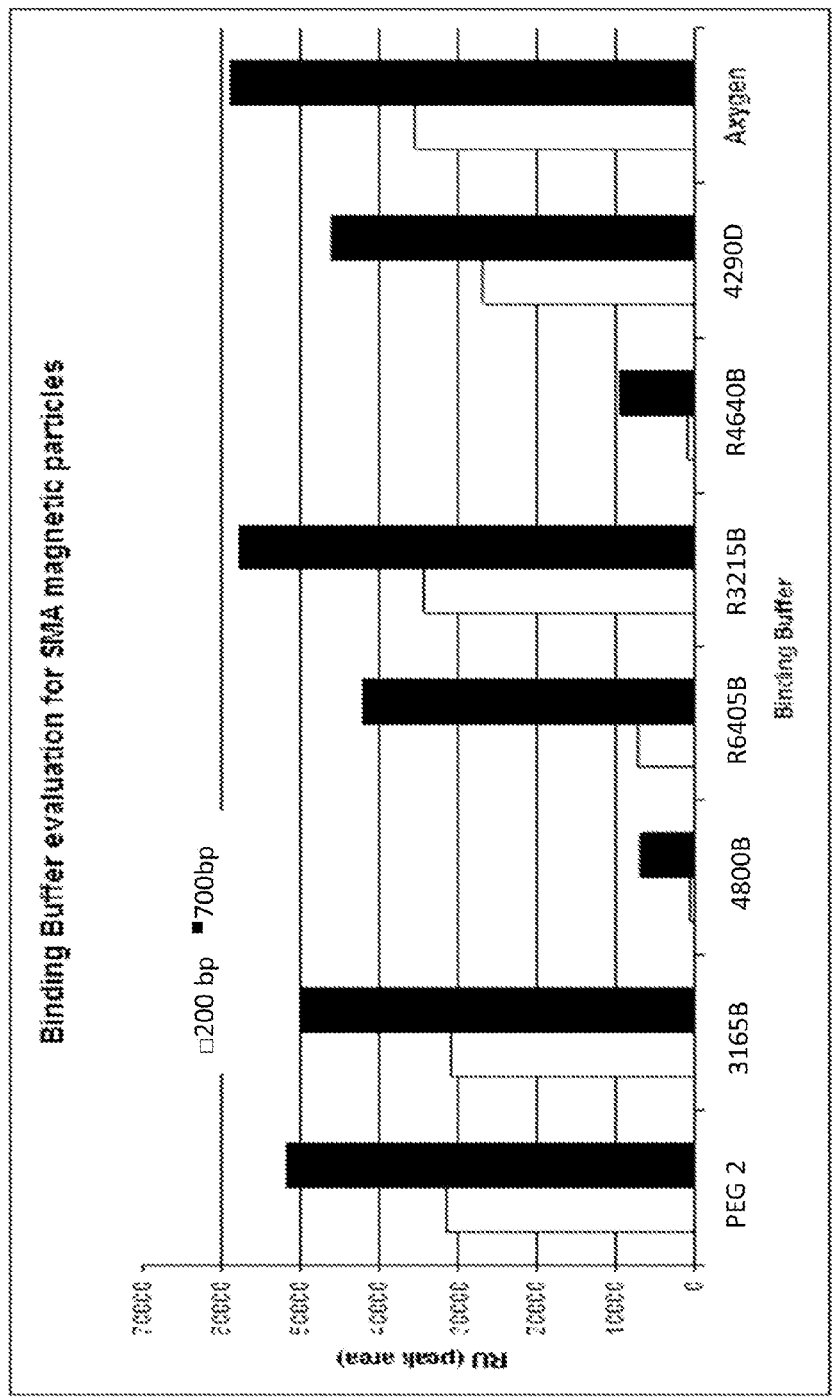
FIG. 3 is a graph showing binding buffer performance (as measured by released DNA as measured by RU) as defined in Tables 1, 2 and 3, with proprietary magnetic particles (Axygen beads), compared to an Axygen buffer control.

FIG. 3 is a graph showing binding buffer performance (as measured by released DNA as measured by RU) as defined in Tables 1, 2 and 3, with proprietary magnetic particles (Axygen beads), compared to an Axygen buffer and PEG2 buffer as controls. FIG. 3 illustrates that Buffers 3165B (Nt/OH=20/3), R6405B (Nt/OH=13/6), R3215B (Nt/OH=15/3) and 4290D (Nt/OH=15/4), and each having an Nt greater than 6, performed comparably to the control buffers. On the other hand, buffers 4800B (Nt/OH=3.5/4) and R4640B (Nt/OH=5/4) having Nt of 3.5 and 5 respectively, did not perform.

Figure 4:
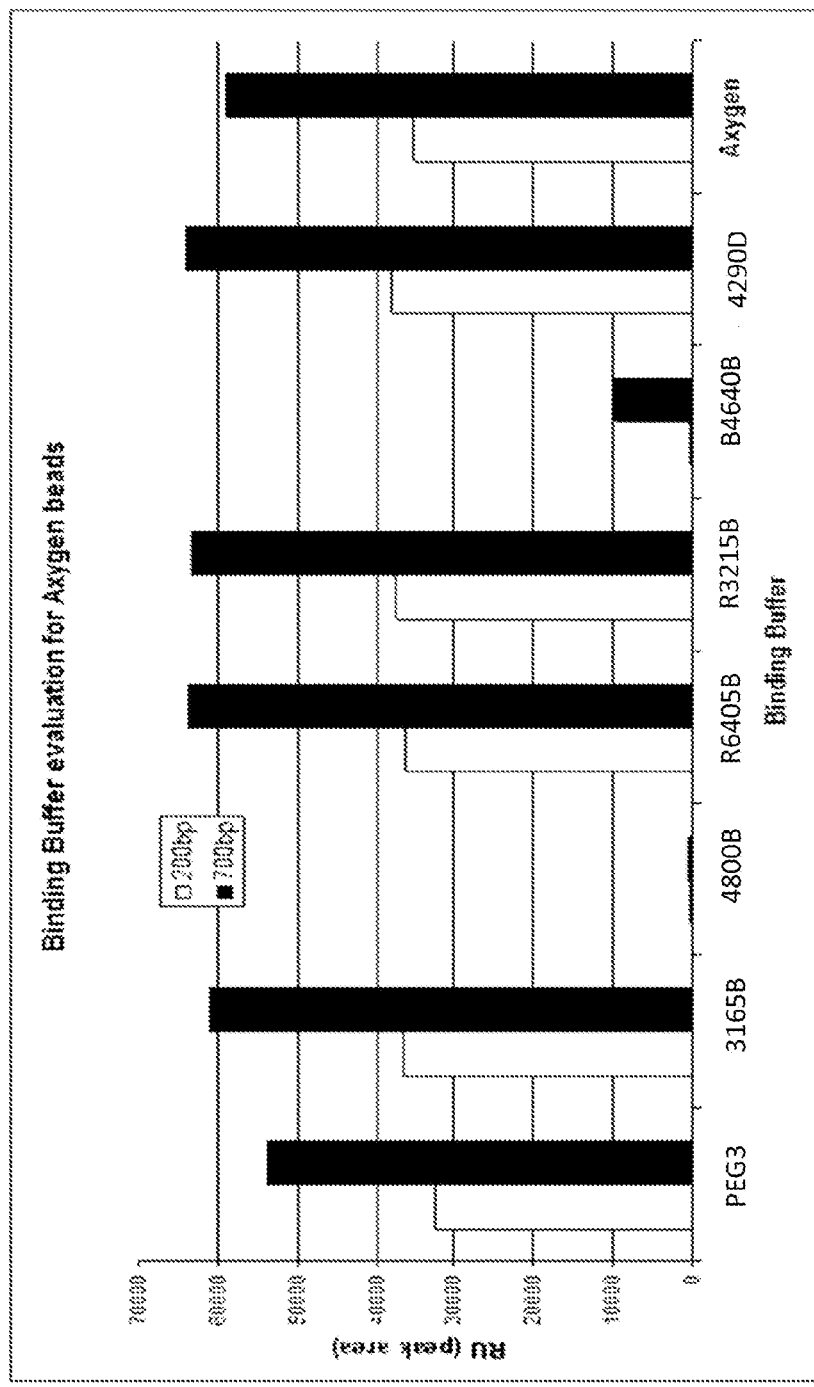
FIG. 4 is a graph showing binding buffer performance (as measured by released DNA as measured by RU) for buffers as defined in Tables 1, 2 and 3 compared to an Axygen buffer control.

FIG. 4 is a graph showing binding buffer performance (as measured by released DNA as measured by RU) using commercially available magnetic beads (available from Axygen, Foster City, Calif.) for buffers as defined in Tables 1, 2 and 3 compared to an Axygen buffer control. FIG. 4 illustrates that Buffers 3165B (Nt/OH=20/3), R6405B (Nt/OH=13/6), R3215B (Nt/OH=15/3) and 4290D (Nt/OH=15/4), and each having an Nt greater than 6, performed comparably to the control buffers, using commercially available beads. On the other hand, buffers 4800B (Nt/OH=3.5/4) and R4640B (Nt/OH=5/4) having Nt of 3.5 and 5 respectively, did not perform, using commercially available beads.

The graphs show that the proper polyol additives with salt perform at the same level as the standard PEG/salt buffer solution and as well as a commercially available proprietary binding buffer/magnetic particle systems sold as kits (Axygen, Foster City, Calif.). The results shown with the commercially available Axygen kit is consistent with results seen from other commercially available PCR clean-up kits. Among the polyols tested, polyol 4290, polyol R3215, polyol 3165 and polyol 3215 all show an efficient crowding effect in high salt to enhance DNA capture with both proprietary experimental magnetic particles (SMA magnetic particles) and Axygen's magnetic beads. The performance matches or surpasses the standard PEG—salt butter based performance (see FIGS. 1-4). A 30-40% concentration of the polyol shows the best performance when using polyol 4290. (FIG. 2.) Both proprietary experimental magnetic particles (SMA particles) and commercially available Axygen magnetic beads with a carboxy based surface chemistry work well with the Polyol based binding buffers (FIG. 4 and FIG. 5).

Some of the polyol based binding buffers also shows a DNA size selectivity effect when different ratios (concentrations) of buffer to PCR reaction are used. For example, buffer containing polyol 4290 showed less 200 bp capture and release of smaller DNA particles (200 bp) larger DNA particles (700 bp) at 30% concentration (FIG. 1 and FIG. 2.). This characteristic can be utilized. For example, this characteristic can be used to provide clean-up buffers that preferentially remove DNA particles of a certain particle size from a preparation. Or, for example, combinations of more than one polyol in a buffer solution may be used to optimize a group of sizes of DNA or other biological material to be removed from a preparation. In embodiments, the polyol buffer disclosed herein is optimized to remove certain particle sizes of biological materials from a preparation. In additional embodiments, the polyol buffers disclosed herein contain mixtures of polyols to optimize the ranges of particle sizes to be preferentially removed from a preparation.

The Perstorp Polyols evaluated have a nominal molecular weight of 800, which is an order of magnitude lower than the preferred PEG based buffer. By not using a polymer such as PEG but a multifunctional alcohol whose predominant use is as a multifunctional crosslinker in polyurethane formulations, this invention solves several issues associated with working in high viscosity buffers. One unexpected benefit of this small size multifunctional alcohol over PEG as the crowding agent is, since the buffer viscosity is lower, it washes away more easily as well as allowing for more rapid mixing and magnetic extraction.

PEG and Polyol 3460 were solid or waxy components, and were not soluble. It will be apparent to those skilled in the art that various modifications and variations can be made without departing from the spirit and scope of the claimed invention.

What is claimed is:

1. A buffer for use with a magnetic affinity-binding thermoplastic particle extraction process comprising at least one soluble polyol having a base structure of Formula 3:

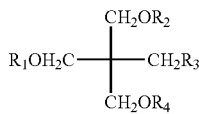

wherein R3 is OH, $CH_3$, $(-OCH_2CH_2O)_nH$, or

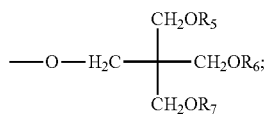

wherein R1, R2, R4, R5, R6 and R7 are each independently H, or $(-CH_2CH_2O)_nH$;
wherein each n is independently an integer of one or greater;
wherein at least one of R1, R2, R4, R5, R6 and R7 is $(-CH_2CH_2O)_nH$;
wherein the total number of $(-CH_2CH_2O)_nH$ groups is $N_t$; and,
wherein $N_t$ is at least 6.

2. The buffer of claim 1 wherein the polyol is alkoxylated pentaerythritol or alkoxylated trimethylolpropane.
3. The buffer of claim 2 wherein the polyol is alkoxylated pentaerythritol or alkoxylated trimethylolpropane.
4. The buffer of claim 1 further comprising magnetic beads.
5. A method of use of the buffer phase of claim 4, comprising:
contacting a substance comprising a biomolecule with the buffer solution of claim 1 such that the solid phase binds the biomolecule through a derivative functional group on the surface of the magnetic beads; and
isolating the biomolecule from the substance.
6. A buffer for use with a magnetic affinity-binding thermoplastic particle extraction process comprising at least one soluble polyol having a base structure of:

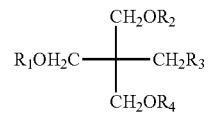

wherein R3 is OH, $CH_3$, $(-OCH_2CH_2O)_nH$, or

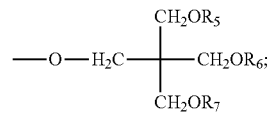

wherein R1, R2, R4, R5, R6 and R7 are each independently H, or $(-CH_2CH_2O)_nH$;
wherein each n is independently an integer of one or greater;
wherein the total number of $(-CH_2CH_2O)_n$ groups is $N_t$;
wherein the polyol has more than two terminal OH groups and
wherein the ratio of terminal OH groups to $N_t$ is greater than 2:1.

7. The buffer of claim 6 wherein $N_t$ is at least 6.
8. The buffer of claim 6 wherein the polyol is alkoxylated pentaerythritol or alkoxylated trimethylolpropane.
9. The buffer of claim 7 wherein the polyol is alkoxylated pentaerythritol or alkoxylated trimethylolpropane.
10. The buffer of claim 6 further comprising magnetic beads.
11. The buffer of claim 7 further comprising magnetic beads.
12. A method of using the buffer of claim 1, comprising:
contacting a substance comprising a biomolecule with the buffer solution of claim 1 such that the magnetic particle binds the biomolecule through a derivative functional group on the surface of the magnetic particle; and
isolating the biomolecule from the substance.
13. A method of using the buffer of claim 6, comprising:
contacting a substance comprising a biomolecule with the buffer solution of claim 6 such that the magnetic particle binds the biomolecule through a derivative functional group on the surface of the magnetic particle; and
isolating the biomolecule from the substance.

* * * * *